United States Patent
Otaka et al.

(10) Patent No.: US 9,687,827 B2
(45) Date of Patent: Jun. 27, 2017

(54) SILICATE-COATED MFI-TYPE ZEOLITE, METHOD OF PRODUCING THE SAME, AND METHOD OF PRODUCING P-XYLENE USING THE SAME

(71) Applicant: JX Nippon Oil & Energy Corporation, Tokyo (JP)

(72) Inventors: Eri Otaka, Tokyo (JP); Yasuhiro Araki, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 142 days.

(21) Appl. No.: 14/389,553

(22) PCT Filed: Mar. 29, 2013

(86) PCT No.: PCT/JP2013/059742
§ 371 (c)(1),
(2) Date: Sep. 30, 2014

(87) PCT Pub. No.: WO2013/147261
PCT Pub. Date: Oct. 3, 2013

(65) Prior Publication Data
US 2015/0328626 A1 Nov. 19, 2015

(30) Foreign Application Priority Data
Mar. 30, 2012 (JP) ................ 2012-083192

(51) Int. Cl.
*B01J 29/40* (2006.01)
*C01B 39/38* (2006.01)
*B01J 37/02* (2006.01)
*B01J 37/10* (2006.01)
*C07C 6/06* (2006.01)
*B01J 29/035* (2006.01)
*B01J 29/00* (2006.01)
*C01B 39/40* (2006.01)
*C07C 6/12* (2006.01)
*B01J 35/02* (2006.01)
*B01J 35/00* (2006.01)

(52) U.S. Cl.
CPC .......... *B01J 29/40* (2013.01); *B01J 29/005* (2013.01); *B01J 29/035* (2013.01); *B01J 35/002* (2013.01); *B01J 35/023* (2013.01); *B01J 37/0215* (2013.01); *B01J 37/10* (2013.01); *C01B 39/38* (2013.01); *C01B 39/40* (2013.01); *C07C 6/06* (2013.01); *C07C 6/123* (2013.01); *B01J 35/0006* (2013.01); *B01J 37/0246* (2013.01); *B01J 2229/16* (2013.01); *B01J 2229/62* (2013.01); *C07C 2529/035* (2013.01); *C07C 2529/40* (2013.01); *C07C 2529/80* (2013.01); *Y02P 20/52* (2015.11)

(58) Field of Classification Search
CPC ........ B01J 29/005; B01J 29/035; B01J 29/40; B01J 35/0006; B01J 35/002; B01J 37/0215; B01J 37/0246; B01J 37/10; B01J 2229/16; B01J 2229/62; C01B 39/38; C01B 39/40; C07C 2529/40; C07C 2529/035; C07C 2529/80
USPC .................. 502/4, 64, 67, 69, 71, 77
See application file for complete search history.

(56) References Cited

U.S. PATENT DOCUMENTS

| | | | |
|---|---|---|---|
| 5,972,203 A | 10/1999 | Smith et al. | |
| 5,994,603 A | 11/1999 | Mohr et al. | |
| 5,998,686 A | 12/1999 | Clem et al. | |
| 6,008,425 A | 12/1999 | Mohr et al. | |
| 6,040,259 A | 3/2000 | Mohr et al. | |
| 6,111,157 A | 8/2000 | Hendriksen et al. | |
| 6,436,869 B1 | 8/2002 | Searle et al. | |
| 6,682,650 B2 * | 1/2004 | Honna | B01J 29/088 208/111.01 |
| 6,831,203 B1 | 12/2004 | Mohr et al. | |
| 8,153,099 B2 | 4/2012 | Yoon et al. | |
| 8,772,564 B2 | 7/2014 | Matsushita et al. | |
| 2002/0082460 A1 * | 6/2002 | Verduijn | B01J 29/80 585/475 |
| 2002/0137977 A1 | 9/2002 | Hendriksen et al. | |
| 2002/0170848 A1 | 11/2002 | Mohr et al. | |
| 2002/0183192 A1 | 12/2002 | Verduijn et al. | |
| 2002/0187891 A1 | 12/2002 | Verduijn et al. | |
| 2003/0027710 A1 | 2/2003 | Smith et al. | |
| 2004/0198586 A1 | 10/2004 | Mohr et al. | |

(Continued)

FOREIGN PATENT DOCUMENTS

| | | |
|---|---|---|
| JP | 59-018112 | 1/1984 |
| JP | 7-252170 | 10/1995 |

(Continued)

OTHER PUBLICATIONS

Database of Zeolite Structures, List of HKL and Intensities—ZSM-5, Calcined MFI, Structure Commission of the International Zeolite Association, 2007, Accessed Jun. 14, 2016, Available online: http:izasc-mirror.la.asu.edu/cgi-bin/collection2.py.*

(Continued)

*Primary Examiner* — Elizabeth Wood
(74) *Attorney, Agent, or Firm* — Wenderoth, Lind & Ponack, L.L.P.

(57) ABSTRACT

A silicate-coated MFI-type zeolite is obtained by coating an MFI-type zeolite with a silicate, and a peak area ratio b/a of a peak b at 2θ=8.4 to 9.7° to a peak a at 2θ=7.0 to 8.4° in an X-ray diffraction spectrum is 1 or more, and a pKa value measured by a Hammett indicator is +3.3 or more.

3 Claims, 9 Drawing Sheets

(56) References Cited

U.S. PATENT DOCUMENTS

| | | |
|---|---|---|
| 2009/0291046 A1 | 11/2009 | Yoon et al. |
| 2011/0201861 A1 | 8/2011 | Bulut et al. |
| 2011/0201863 A1 | 8/2011 | Matsushita et al. |
| 2012/0004487 A1* | 1/2012 | Igarashi .................. B01J 29/40 585/467 |

FOREIGN PATENT DOCUMENTS

| | | |
|---|---|---|
| JP | 2001-031416 | 2/2001 |
| JP | 2001-504084 | 3/2001 |
| JP | 2003-500189 | 1/2003 |
| JP | 2004-002160 | 1/2004 |
| JP | 2010-221095 | 10/2010 |
| JP | 2011-523619 | 8/2011 |
| KR | 10-2009-0120846 | 11/2009 |
| KR | 10-2011-0066933 | 6/2011 |
| WO | 2010/107076 | 9/2010 |

OTHER PUBLICATIONS

Korean Office Action issued Nov. 17, 2015 in corresponding Korean Patent Application No. 10-2014-7027596.
International Search Report issued May 21, 2013 in International (PCT) Application No. PCT/JP2013/059742.
Y. Osafune et al., "Core-Shell no MFI-gata Zeolite o Shokubai ni Mochiita Toluene no Methyl-ka", Proceedings of $102^{nd}$ Catalyst Debate A, p. 213, Sep. 23, 2008 (English abstract).

* cited by examiner

US 9,687,827 B2

SILICATE-COATED MFI-TYPE ZEOLITE, METHOD OF PRODUCING THE SAME, AND METHOD OF PRODUCING P-XYLENE USING THE SAME

FIELD

The present invention relates to a silicate-coated MFI-type zeolite, a method of producing the same, and a method of producing p-xylene by a disproportionation reaction or an alkylation reaction of an aromatic hydrocarbon, especially toluene using a catalyst including the zeolite. In particular, the present invention relates to a method of producing high purity p-xylene in a high yield.

BACKGROUND

Among aromatic compounds, xylenes are very important compounds which serve as a starting material for production of terephthalic acid, isophthalic acid, orthophthalic acid, or the like, which is a starting material for polyester, and are produced by various production methods. In particular, p-xylene is useful as a starting material for production of terephthalic acid which is a monomer starting material for polyethylene terephthalate. Various methods for selectively producing p-xylene have been proposed.

In order to selectively produce p-xylene from an aromatic hydrocarbon (for example, toluene), use of molecular sieving action (or shape selectivity) of an MFI-type zeolite has been studied. However, particularly an MFI-type zeolite whose outer surface has not been treated has active sites (acid sites) inside pores and on the outer surface. When a reaction occurs inside the pores, the shape selectivity is expressed by diffusion restriction due to the molecular size of a product, and only p-xylene is obtained. In contrast, when a reaction occurs on the outer surface, the shape selectivity is not expressed, and other isomers (o-xylene and m-xylene) are also produced. Further, when p-xylene produced inside the pores comes into contact with the acid sites on the outer surface, a reaction of isomerizing p-xylene into o-xylene and m-xylene also occurs. In the MFI-type zeolite whose outer surface has not been treated, a reaction occurs predominantly on the outer surface. Therefore, a product is usually a mixture of o-, m-, and p-xylenes, and the selectivity of p-xylene under thermodynamic equilibrium is about 23%. Accordingly, in order to selectively obtain only p-xylene, it is necessary to use only the active sites inside the pores of the MFI-type zeolite. A technique of removing aluminum that is an active site (acid site) on the outer surface and a technique of coating or modifying aluminum have been proposed.

Patent Literature 1 discloses that p-xylene can be produced by a reaction of toluene with a methylating agent in the presence of a zeolite bound zeolite catalyst containing a first zeolite having an MFI structure and a second zeolite in which the first zeolite is at least partially coated and which has an MFI structure.

Patent Literature 2 discloses a catalyst which is suitable for hydrocarbon conversion, contains a first porous inorganic material of ZSM-5, and has an outside face of a macrostructure having a three-dimensional structure, part of which is coated with a second porous inorganic material of silicalite.

Patent Literature 3 discloses a catalyst in which the outer surface of an MFI-type zeolite having a predetermined crystallite diameter is modified with a silicate having a specific thickness to coat aluminum which is an active site.

A catalyst has also been proposed in which an MFI-type zeolite is synthesized by introduction of a fluorine source, and the synthesized MFI-type zeolite is hydrothermally synthesized with a fluorine source and a silica source to form a silicate film on the outer surface of the MFI-type zeolite (see Non Patent Literature 1).

On the other hand, Patent Literature 4 discloses a catalyst in which an MFI-type zeolite having predetermined $SiO_2$/$Al_2O_3$ ratio and a primary particle diameter is coated with a crystalline silicate and a pKa value at an acid site on the outer surface of the catalyst is regulated by a Hammett indicator.

CITATION LIST

Non Patent Literature

Non Patent Literature 1: Yukio Osafune et al., Proceedings of 102nd Catalyst Debate A, p. 213, published on 23 Sep. 2008

Patent Literature

Patent Literature 1: Japanese National Publication of International Patent Application No. 2001-504084
Patent Literature 2: Japanese National Publication of International Patent Application No. 2003-500189
Patent Literature 3: Japanese Patent Application Laid-open No. 2010-221095
Patent Literature 4: WO2010/107076

SUMMARY

Technical Problem

The MFI-type zeolite having a modified outer surface allows p-xylene to be produced at a high selectivity by an alkylation reaction of benzene and/or toluene. However, the acid site (aluminum) on the outer surface of the MFI-type zeolite having a modified outer surface is not sufficiently coated, and therefore high p-xylene selectivity can be achieved only under a condition of diluted starting material. Accordingly, a problem of low yield of p-xylene occurs. Further, since the MFI-type zeolite having a modified outer surface can be used only under a condition of diluted starting material, it is difficult that p-xylene is produced in a high yield by a toluene disproportionation reaction that has a reactivity lower than that of an alkylation reaction of toluene. Therefore, production of p-xylene by the toluene disproportionation reaction using the catalyst is not suitable in practical terms.

The present invention has been made in view of the above circumstances, and provides a silicate-coated MFI-type zeolite that allows p-xylene to be selectively produced in a high yield by an alkylation reaction or a disproportionation reaction of an aromatic hydrocarbon, especially toluene, a method of producing the silicate-coated MFI-type zeolite, and a method of producing p-xylene.

Solution to Problem

The present inventors have extensively investigated to achieve an object described above, and as a result, found that when a silicate-coated MFI-type zeolite in which a specific MFI-type zeolite is coated with a silicate, a peak area ratio b/a of a peak b at 2θ=8.4 to 9.7° to a peak a at 2θ=. 7.0 to 8.4° in an X-ray diffraction spectrum is 1 or more, and a pKa value measured by a Hammett indicator is +3.3 or more is used in a disproportionation reaction or an alkylation reaction of an aromatic hydrocarbon, especially toluene, high purity p-xylene can be produced in a high yield. Thus, the present, invention has been completed.

That is, a silicate-coated MFI-type zeolite according to the present invention is obtained by coating an MFI-type zeolite with a silicate, wherein a peak area ratio b/a of a peak b at 2θ=8.4 to 9.7° to a peak a at 2θ=7.0 to 8.4° in an X-ray diffraction spectrum of the silicate-coated MFI-type zeolite is 1 or more and a pKa value measured by a Hammett indicator is +3.3 or more.

Moreover, in the above-described silicate-coated MFI-type zeolite according to the present invention, a peak area ratio b'/a' of a peak b' at 2θ=8.4 to 9.7° to a peak a' at 2θ=7.0 to 8.4° in an X-ray diffraction spectrum of the MFI-type zeolite is 1 or more. Here, in the ranges of 2θ=7.0 to 8.4° and 2θ=8.4 to 9.7°, the peaks a and b of the MFI-type zeolite coated with a silicate are distinguished from the peaks a' and b' of the MFI-type zeolite before being coated with a silicate.

Moreover, in the above-described silicate-coated MFI-type zeolite according to the present invention, an amount of aluminum in sites other than a skeleton of the MFI-type zeolite is 10% or less.

Moreover, in the above-described silicate-coated MFI-type zeolite according to the present invention, a particle diameter is 1 μm or larger and 40 m or smaller.

Moreover, the above-described silicate-coated MFI-type zeolite according to the present invention is used to selectively produce p-xylene by a disproportionation reaction or an alkylation reaction of an aromatic hydrocarbon, especially toluene.

Moreover, a method of producing one of the above-described silicate-coated MFI-type zeolites according to the present invention includes synthesizing hydrothermally an MFI-type zeolite having an peak area ratio b'/a' of a peak b' at 2θ=8.4 to 9.7° to a peak a' at 2θ=7.0 to 8.4° of 1 or more using a silica source and a structure directing agent to allow a silicate to grow on an outer surface of the MFI-type zeolite.

Moreover, in the above-described method of producing the silicate-coated MFI-type zeolite according to the present invention, the MFI-type zeolite is obtained by a hydrothermal synthesis treatment using a silica source, an aluminum source, a structure directing agent, and a fluorine source.

Moreover, the above-described method of producing the silicate-coated MFI-type zeolite according to the present invention includes removing aluminum in sites other than a skeleton of the MFI-type zeolite.

Moreover, a method of producing p-xylene according to the present invention includes: bringing the silicate-coated MFI-type zeolite of any one of claims 1 to 5 into contact with an aromatic hydrocarbon; and causing a disproportionation reaction or an alkylation reaction to selectively produce p-xylene.

Advantageous Effects of Invention

Since the silicate-coated MFI-type zeolite of the present invention is an MFI-type zeolite having an outer surface coated with an inert silicate, the silicate-coated MFI-type zeolite can be suitably used to selectively produce p-xylene utilizing a molecular sieving action (or shape selectivity) of the MFI-type zeolite. In particular, when a silicate-coated MFI-type zeolite having a peak area ratio b/a of a peak b at 2θ=8.4 to 9.7° to a peak a at 2θ=7.0 to 8.4° in an X-ray diffraction spectrum of 1 or more, and a pKa value measured by a Hammett indicator of +3.3 or more is used, a zeolite that suppresses a reaction at an acid site on the outer surface of an MFI-type zeolite having no shape selectivity and allows p-xylene to be selectively produced in a high yield by an alkylation reaction or a disproportionation reaction of an aromatic hydrocarbon, especially toluene can be provided.

DESCRIPTION OF EMBODIMENTS

Figure 1:
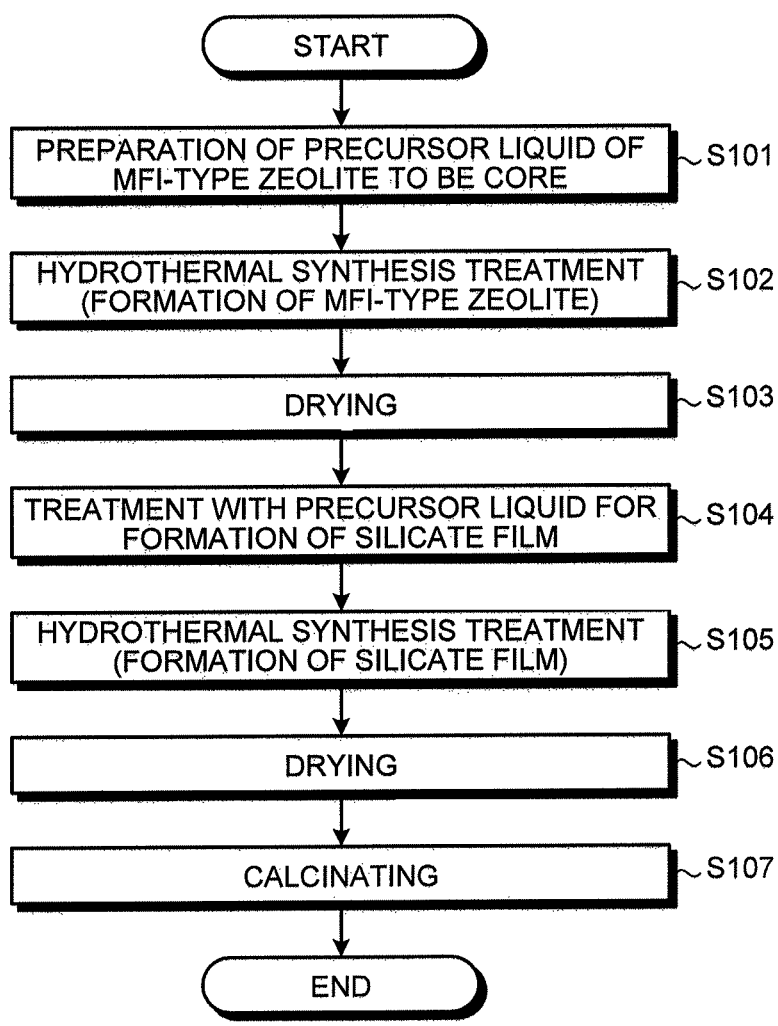
FIG. 1 is a flow chart of a process of producing a silicate-coated MFI-type zeolite of the present invention.
Figure 2:
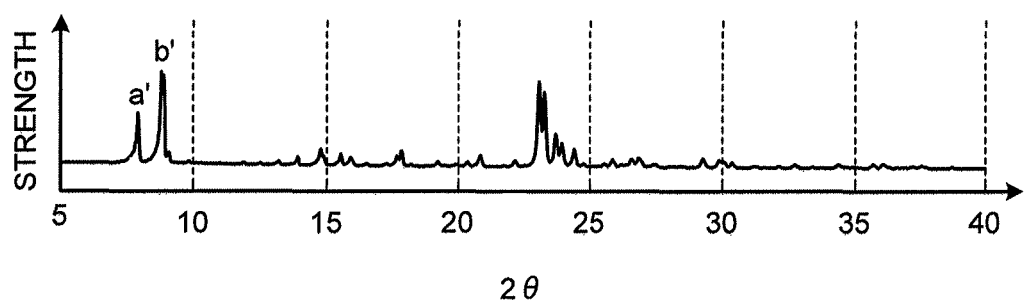
FIG. 2 is an X-ray diffraction chart of a ZSM-5 type zeolite according to Synthesis Example 1.
Figure 3:
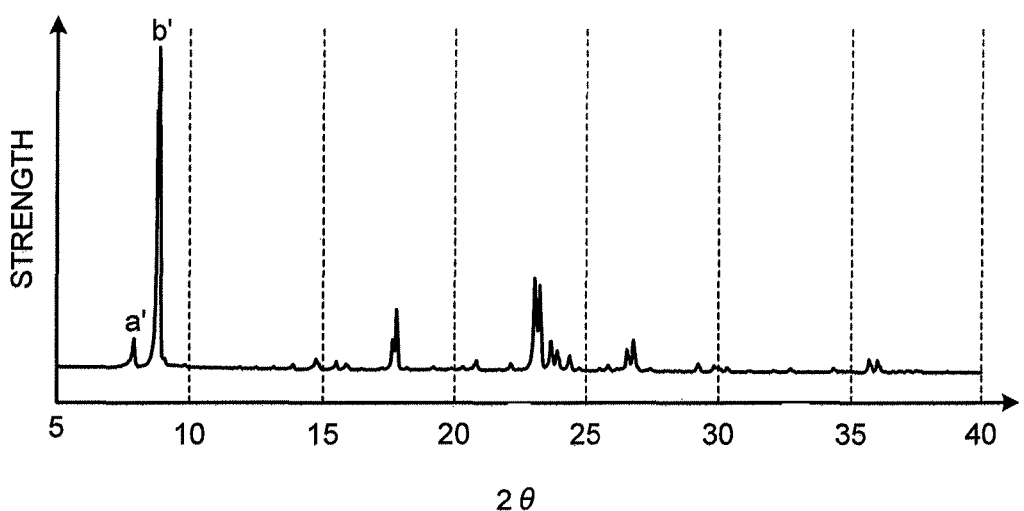
FIG. 3 is an X-ray diffraction chart of a ZSM-5 type zeolite according to Synthesis Example 2.
Figure 4:
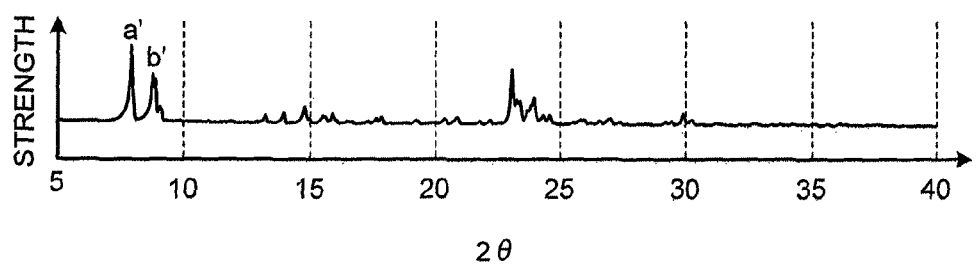
FIG. 4 is an X-ray diffraction chart of a ZSM-5 type zeolite according to Synthesis Example 3.
Figure 5:
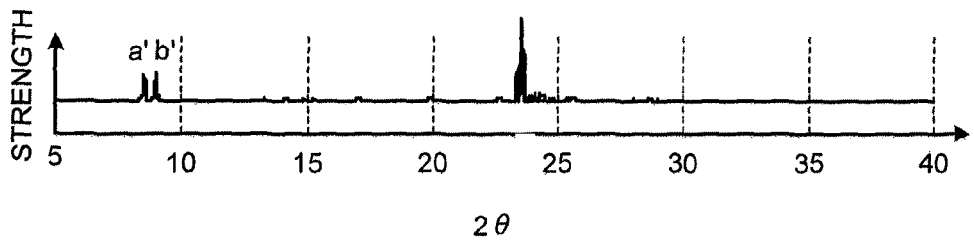
FIG. 5 is an X-ray diffraction chart of a ZSM-5 type zeolite according to Synthesis Example 4.
Figure 6:
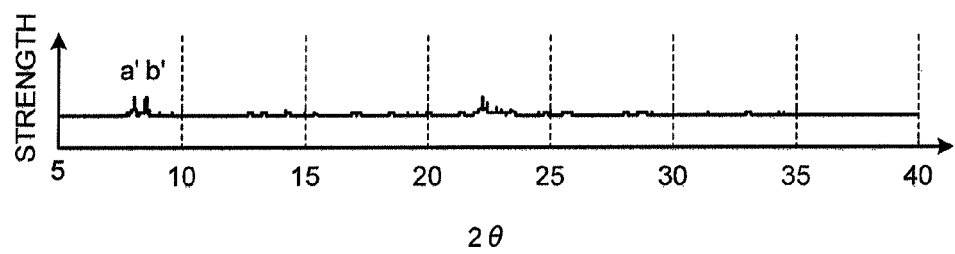
FIG. 6 is an X-ray diffraction chart of a ZSM-5 type zeolite according to Synthesis Example 5.

The present inventors have found that when a silicate-coated MFI-type zeolite having a peak area ratio b/a of a peak b at 2θ=8.4 to 9.7° to a peak a at 2θ=7.0 to 8.4° in an X-ray diffraction spectrum of 1 or more, and a pKa value measured by a Hammett indicator of +3.3 or more is used in a disproportionation reaction or an alkylation reaction of an aromatic hydrocarbon, especially toluene, p-xylene can be produced at a high selectivity in a high yield.

Hereinafter, a silicate-coated MFI-type zeolite and a method of producing the silicate-coated MFI-type zeolite according to an embodiment of the present invention will be described in detail with reference to the drawings and the like. The present invention is not limited to this embodiment.

<Silicate-Coated MFI-Type Zeolite>

In the silicate-coated MFI-type zeolite of the present invention, the peak area ratio b/a of the peak b at 2θ=8.4 to 9.7° to the peak a at 2θ=7.0 to 8.4° in an X-ray diffraction spectrum is 1 or more, and the pKa value measured by a Hammett indicator is +3.3 or more. The peak area ratio b/a is more preferably 1.4 or more, and further preferably 1.9 or more. When the peak area ratio b/a is 1 or more, the thickness of zeolite crystal in a direction of pores in which a starting material and a product tend to be diffused is relatively small. Therefore, the reaction rate increases, and p-xylene can be produced in a high yield. The pKa value of the silicate-coated MFI-type zeolite measured by a Hammett indicator is +3.3 or more. For this reason, an acid site on the outer surface having no shape selectivity is coated with a silicate inert to a reaction. When the silicate-coated MFI-type zeolite is used in a disproportionation reaction or an alkylation reaction of an aromatic hydrocarbon, especially toluene, p-xylene can be produced at a high selectivity.

In the present invention, an X-ray diffraction chart is obtained under the following conditions. The following conditions are not limited as long as an X-ray diffraction chart can be obtained and are not meant to limit an X-ray diffraction device.

Device: Ultima IV manufactured by Rigaku Corporation
X-ray source: CuKα1
Tube power: 30 kV
Tube current: 20 mA
Scan rate: 4°/min
Step width: 0.02°

The peak area herein means an integrated intensity of a peak in an X-ray diffraction chart. In an X-ray diffraction spectrum of a silicate-coated MFI-type zeolite, the peak at 2θ=7.0 to 8.4° is defined as a peak a, and the peak at 2θ=8.4 to 9.7° is defined as a peak b. In an X-ray diffraction spectrum of an MFI-type zeolite to form a core before being coated with a silicate (also referred to as MFI-type zeolite or MFI-type zeolite before being coated with a silicate), the peak at 2θ=7.0 to 8.4° is defined as a peak a', and the peak at 2θ=8.4 to 9.7° is defined as a peak b'.

In an MFI-type zeolite before being coated with a silicate of the present invention, the peak area ratio b'/a' of the peak b' at 2θ=8.4 to 9.7° to the peak a' at 2θ=7.0 to 8.4° in an X-ray diffraction spectrum is preferably 1 or more. The peak area ratio b'/a' is more preferably 2 or more, further preferably 5 or more, and particularly preferably 9 or more. When the peak area ratio b'/a' is 1 or more, the thickness of zeolite crystal in a direction of pores in which a starting material and a product tend to be diffused is relatively small. Even when the outer surface of the MFI-type zeolite is coated with a silicate, the reaction rate hardly decreases, and p-xylene can be produced in a high yield. When an MFI-type zeolite having a peak area ratio b'/a' of 1 or more is coated with a silicate, a silicate film is likely to grow on the outer surface. Therefore, the silicate film is uniform and has almost no defects. When the silicate-coated MFI-type zeolite is used in a disproportionation reaction or an alkylation reaction of an aromatic hydrocarbon, especially toluene, p-xylene can be produced at a high selectivity.

For the MFI-type zeolite before being coated with a silicate of the present invention, ZSM-5, TS-1, TSZ, SSI-10, USC-4, NU-4; or the like can be suitably used. ZSM-5 is particularly preferable. Since these MFI-type zeolites have pores having the same size (about 0.55 nm) as the shortest diameter of a p-xylene molecule, p-xylene can be distinguished from o-xylene and m-xylene, which have a molecular size slightly larger than that of p-xylene. For this reason, they are particularly effective in production of target p-xylene.

The silica/alumina ratio ($SiO_2/Al_2O_3$ ratio by mole) of the MFI-type zeolite before being coated with a silicate of the present invention is preferably 24 or more and 500 or less, more preferably 24 or more and 100 or less, and further preferably 24 or more and 70 or less. In order to stably hold an MFI structure, the silica/alumina ratio is preferably 24 or more. In order to hold the amount of acid (aluminum) that is a reaction active site, the silica/alumina ratio is preferably 500 or less.

In the silicate-coated MFI-type zeolite of the present invention, the outer surface of the MFI-type zeolite is coated with a silicate. The silicate may be amorphous, but is preferably crystalline (specific examples may include a crystalline silicate), and more preferably a crystalline silicate having a crystal structure similar to that of the MFI-type zeolite to form a core and pores that form continuous layers (specific examples may include silicalite). When the silicate has a crystal structure similar to that of the MFI-type zeolite and pores that form continuous layers, the pores of the MFI-type zeolite that are reaction sites are hardly closed. Therefore, diffusion of a starting material, a product, and the like inside zeolite particles is not inhibited, and the conversion ratio in a reaction tends to be improved as compared with a case of coating the zeolite with an amorphous silicate. The silicate is desirably inert to an alkylation reaction and a disproportionation reaction of an aromatic hydrocarbon (especially toluene), and is preferably pure silica containing no aluminum.

In the silicate-coated MFI-type zeolite of the present invention, the peak area ratio b/a of the peak b at 2θ=8.4 to 9.7° to the peak a at 2θ=7.0 to 8.4° in an X-ray diffraction spectrum is 1 or more. In the silicate-coated MFI-type zeolite having a peak area ratio b/a of such a range, a silicate film is uniform and has almost no defects. When the silicate-coated MFI-type zeolite is used in a disproportionation reaction or an alkylation reaction of an aromatic hydrocarbon, especially toluene, p-xylene can be produced at a high selectivity in a high yield.

In the silicate-coated MFI-type zeolite of the present invention, the pKa value measured by a Hammett indicator is particularly preferably +3.3 or more. When the pKa value of the silicate-coated MFI-type zeolite is +3.3 or more, the outer surface is inert to a disproportionation reaction, an alkylation reaction, and an isomerization reaction of an aromatic hydrocarbon, and a shape selective reaction can be effectively performed.

The silica/alumina ratio ($SiO_2/Al_2O_3$ ratio by mole) of a zeolite portion that is a core of the silicate-coated MFI-type zeolite of the present invention is not limited to a range capable of holding an MFI-type structure, and is preferably 24 or more and 500 or less, more preferably 24 or more and 100 or less, and further preferably 24 or more and 70 or less. In order to stably hold an MFI structure, the silica/alumina ratio is preferably 24 or more. In order to hold the amount of acid (aluminum) that is a reaction active site, the silica/alumina ratio is preferably 500 or less.

<Performance Evaluation by Measuring pKa Value by Hammett Indicator>

The pKa value measured by a Hammett indicator is an index showing acid and base strengths, and general explanation and measurement method are described in a book in detail. Specifically, a pKa value of +7.0 means neutrality, a pKa value higher than +7.0 means stronger base strength, and a pKa value lower than +7.0 means stronger acid strength.

In measurement of specific pKa value in the present invention, a spectrophotometer may be used. Specifically, 0.25 g of a silicate-coated MFI-type zeolite is added to 7 mL of a solution of a Hammett indicator in dehydrated benzene with a predetermined concentration (each concentration is shown in Table 1), and a change in the color of the silicate-coated MFI-type zeolite, that is, a coloring degree due to a change in the color of the Hammett indicator is determined by a spectrophotometer. Thus, the measurement is performed. Here, a* and b* coordinate values in an L*a*b* color system defined in accordance with Japan Industrial Standard JIS Z 8729 are measured by a spectrophotometer to observe a change in the color (coloring degree).

A Hammett indicator used for the measurement of pKa value in the present invention includes 2,4-dinitrotoluene (pKa: −13.75), p-nitrotoluene (pKa: −11.35), anthraquinone (pKa: −8.2), benzalacetophenone (pKa: −5.6), dicinnamalacetone (pKa: −3.0), benzeneazodiphenylamine (pKa: +1.5), p-dimethylaminoazobenzene (pKa: +3.3), 4-(phenylazo)-1-naphthylamine (pKa: +4.0), methyl red (pKa: +4.8), and neutral red (pKa: +6.8). Since the Hammett indicator is a molecule that does not enter pores of the MFI-type zeolite, it reacts with only an acid site on the outer surface of the zeolite to cause a change in the color. An index of deciding that the color of the Hammett indicator is changed by the zeolite (the zeolite is colored) is a timing when a color difference (Δa* or Δb*) between the zeolite and high-purity silica (NIPGEL AZ-200 available from TOSOH SILICA CORPORATION) not causing a change in the color of the Hammett indicator during addition to a solution of each Hammett indicator shown in Table 1 becomes a value shown in Table 1. Table 1 shows the index of deciding coloring of the Hammett indicator. In decision of this coloring, when the zeolite causes a change in the color of a Hammett indicator having a pKa of X and is colored, the pKa value of the zeolite is decided to be less than X. When the zeolite does not cause a change in the color of a Hammett indicator having a pKa of Y, the pKa value of the zeolite is decided to be Y or more. Therefore, a pKa value measured by a Hammett indicator of +3.3 or more means that the color of p-dimethylaminoazobenzene (pKa: +3.3) is not changed.

TABLE 1

| Hammett indicator | pKa value | Concentration [G/L] | Value decided to be colored |
|---|---|---|---|
| p-Nitrotoluene | −11.35 | 1.0 | Δb* ≥ 6 |
| Anthraquinone | −8.2 | 1.0 | Δb* ≥ 3.5 |
| Βενζαλαχετοπηενονε | −5.6 | 1.0 | Δb* ≥ 5 |
| Dicinnamalacetone | −3.0 | 0.01 | Δb* ≥ 6 |
| Benzeneazodiphenylamine | +1.5 | 0.001 | Δb* ≥ −6 |
| π-Διμετηψλαμινοαζοβενζενε | +3.36 | 0.01 | Δb* ≥ 9 |

A method of producing the silicate-coated MFI-type zeolite of the present invention is not particularly limited as long as the area ratio b/a of the peak b at 2θ=8.4 to 9.7° to the peak a at 2θ=7.0 to 8.4° in an X-ray diffraction spectrum is 1 or more and the pKa value measured by a Hammett indicator is +3.3 or more. For example, the following method of producing the silicate-coated MFI-type zeolite can preferably be exemplified.

<Method of Producing Silicate-Coated MFI-Type Zeolite>
(Preparation of Core—Structure Directing Agent)

In a method of producing the silicate-coated MFI-type zeolite of the present invention, it is preferable that the MFI-type zeolite to form a core be crystallized using a structure directing agent such as tetrapropylammonium bromide (TPABr), tetrapropylammonium hydroxide (TPAOH), and tetraethylammonium hydroxide (TPABr). Among them, tetrapropylammonium bromide (TPABr) is more preferably used as a structure directing agent.

(Preparation of Core—Si Source, Al Source, F Source, Mineralizer, and the Like)

As a silica source used in synthesis of the MFI-type zeolite to form a core, amorphous silica, amorphous silica, fumed silica, colloidal silica, tetraethyl orthosilicate (TEOS), sodium silicate, potassium silicate, lithium silicate, or the like can be used.

As an aluminum source, sodium aluminate, potassium aluminate, aluminum chloride, aluminum nitrate, aluminum sulfate, aluminum hydroxide, or the like can be used.

In addition to the silica source and the aluminum source, the MFI-type zeolite to form a core may be crystallized in the presence of fluoride ions. As a fluorine source that gives fluoride ions in an aqueous solution, ammonium fluoride, hydrogen fluoride, or the like may be used since it is expected to obtain an MFI-type zeolite having a peak area ratio b'/a' of the peak b' at 2θ=8.4 to 9.7° to the peak a' at 2θ=7.0 to 8.4° of 1 or more in an X-ray diffraction spectrum of the MFI-type zeolite.

In synthesis using no fluorine source, it is preferable that only TEOS be used as the silica source. The reason for this is not clear, but this is because in synthesis of the MFI-type zeolite using only TEOS as the silica source, the area ratio b'/a' of the peak b' at 2θ=8.4 to 9.7° to the peak a' at 2θ=7.0 to 8.4° in an X-ray diffraction spectrum of the synthesized MFI-type zeolite tends to be 1 or more. When the MFI-type zeolite is synthesized using a fluorine source, it is preferable that fumed silica be used as the silica source. The reason for this is not clear, but this is because in synthesis of the MFI-type zeolite using fumed silica and a fluorine source in combination, the area ratio b'/a' in an X-ray diffraction spectrum of the synthesized MFI-type zeolite tends to be 1 or more.

According to a composition of a target MFI-type zeolite, the MFI-type zeolite to form a core may be crystallized in the presence of a mineralizer. As the mineralizer, a hydroxide of alkali metal or alkaline earth metal can be used. Specific examples thereof may include sodium hydroxide.

(Preparation of Core—Hydrothermal Synthesis)

It is preferable that the MFI-type zeolite to form a core be crystallized by hydrothermal synthesis or the like. A hydrothermal synthesis treatment can be performed by a general method, for example, by mixing a silica source, an aluminum source, a fluorine source, a mineralizer, and a structure directing agent in water or an aqueous alcohol solution to prepare a precursor liquid, and introducing the obtained precursor liquid into an autoclave, followed by heating. The temperature of the hydrothermal synthesis treatment is preferably 100° C. or higher and 250° C. or lower, and more preferably 150° C. or higher and 200° C. or lower. The time of the hydrothermal synthesis treatment is preferably 0.5 hours or more and 120 hours or less, more preferably 1 hour or more and 100 hours or less, and further preferably 10 hours or more and 100 hours or less. The hydrothermal synthesis treatment may be performed a plurality times.

It is preferable that a crystallized core be dried at 80 to 140° C., and the outer surface of the core be then coated with a silicate without a calcination (without calcinating history). When the crystallized core is not calcinated, it is expected to obtain an MFI-type zeolite in which the peak area ratio b'/a' of the peak b' at 2θ=8.4 to 9.7° to the peak a' at 2θ=7.0 to 8.4° is 1 or more in an X-ray diffraction spectrum.

When a mineralizer is used in preparation of the MFI-type zeolite to form a core, the MFI-type zeolite may be subjected to an ion-exchange treatment before the outer surface of the core is coated with a silicate. The ion-exchange treatment herein means that a zeolite is converted into a proton-type zeolite. A zeolite is converted into an ammonium-type zeolite by replacement of alkali metal ions or the like by ammonium ions, and the zeolite is calcinated to be converted into a proton-type zeolite. As a result, activity is expressed. Examples of an ammonium ion source may include ammonium nitrate and ammonium chloride. In the ion-exchange treatment, the crystallized core is dried at 80 to 140° C., and calcinated at 450° C. to 700° C. for 2 to 10 hours, and the zeolite is added to an aqueous solution containing ammonium ions at room temperature to 100° C., stirred for 10 minutes to 1 day, and filtered off. Subsequently, the zeolite is dried at 80 to 140° C., and further calcinated at 250 to 600° C. for 0.5 to 10 hours, to be converted into a proton-type zeolite. In order to decrease a production process in terms of cost reduction, the zeolite may be coated with a silicate without a calcination after ion exchange followed by drying.

When aluminum derived from sites other than a zeolite skeleton is present in the pores and on the outer surface of the MFI-type zeolite to form a core, the aluminum is solved during coating with a silicate, and incorporated into the outer surface of the zeolite to express an acid site. Therefore, This is not preferable. The proportion of aluminum derived from sites other than a zeolite skeleton among all aluminum contained in the MFI-type zeolite to form a core is preferably 10% or less, more preferably 5% or less, and further preferably 1% or less.

A method of removing aluminum contained in the sites other than a zeolite skeleton is not particularly limited. Examples thereof may include a method in which a zeolite is added to water at 50 to 100° C., stirred for 10 minutes to 1 day, and filtered off followed by drying at 80 to 140° C. Alternatively, aluminum in the sites other than a zeolite skeleton can be removed even by the ion-exchange treatment described above. When aluminum contained in the sites other than a zeolite skeleton is removed by the ion-exchange treatment, ion exchange can be performed at the same time. Therefore, this is more preferable.

(Silicate Coating)

A silicate with which the MFI-type zeolite to form a core is coated is desirably inert to a disproportionation reaction and an alkylation reaction of an aromatic hydrocarbon, especially toluene, and is preferably pure silica (for example, silicalite) containing no alumina component (active component). Since pure silica has almost no acid sites, the surface of the MFI-type zeolite coated can be made inert to a disproportionation reaction and the like. When the MFI-type zeolite is uniformly coated with pure silica without defects, a disproportionation reaction, an isomerization reaction, and the like on the outer surface can be suppressed, and only a reaction corresponding to a molecular sieve size of inside of the pores can be caused.

The mass of a silicate film is preferably 1 part by mass or more and 100 parts by mass or less relative to 100 parts by mass of the MFI-type zeolite to form a core. When the mass of the silicate film is less than 1 part by mass relative to 100 parts by mass of the MFI-type zeolite to form a core, the molecular sieving action of the silicate film cannot be sufficiently exerted. This is not preferable. When the mass of the silicate film is more than 100 parts by mass relative to 100 parts by mass of the MFI-type zeolite to form a core, the proportion of the MFI-type zeolite to form a core in a catalyst decreases, and the resistance of a starting material and a product that pass through the silicate film increases to decrease the conversion ratio in a reaction. This is not preferable. The mass of the silicate film is particularly preferably 10 parts by mass or more and 70 parts by mass or less relative to 100 parts by mass of the MFI-type zeolite to form a core.

The particle diameter of the silicate-coated MFI-type zeolite according to the present invention is preferably 1 μm or larger and 40 μm or smaller, and more preferably 1 μm or larger and 25 μm or smaller. This is because when a silicate-coated MFI-type zeolite has a particle diameter of larger than 40 μm, the length of pores of silicate-coated MFI-type zeolite increases, the diffusion rate of reaction substrate (starting material) in the pores lowers, and a practical conversion ratio cannot be obtained. Further, this is because when a silicate-coated MFI-type zeolite has a particle diameter of smaller than 1 μm, the MFI-type zeolite to form a core may aggregate, and it is difficult to uniformly coat the zeolite with a silicate.

(Silicate Coating—Preparation of Precursor Liquid for Formation of Silicate Film)

A method of coating the MFI-type zeolite to form a core with a silicate is not limited to a method described below. A hydrothermal synthesis method can be used. For example, a silica source including tetraethyl orthosilicate (TEOS), fumed silica, and colloidal silica, and a structure directing agent including tetrapropylammonium bromide (TPABr) and tetrapropylammonium hydroxide (TPAOH) as starting materials are dissolved in water or an aqueous alcohol solution to prepare a precursor liquid for formation of a silicate film. In this case, it is preferable that the precursor liquid do not contain a fluoride ion. In the precursor liquid for formation of a silicate film, it is preferable that the silica source in an amount of 0.5 to 5 mol in terms of oxide relative to 120 mol of water and the structure directing agent in an amount of 0.01 to 0.5 mol in terms of oxide relative to 120 mol of water be mixed.

(Silicate Coating—Hydrothermal Synthesis)

An autoclave charged with the MFI-type zeolite to form a core and the precursor liquid for formation of a silicate film is placed in an oven, and heated to perform hydrothermal synthesis. The temperature of the hydrothermal synthesis treatment is preferably 100° C. or higher and 250° C. or lower, and more preferably 150° C. or higher and 200° C. or lower. The time of the hydrothermal synthesis treatment is preferably 0.5 hours or longer and 48 hours or shorter, and more preferably 1 hour or longer and 36 hours or shorter.

(Calcination of Silicate-Coated MFI-Type Zeolite)

After the hydrothermal synthesis treatment, the silicate-coated MFI-type zeolite is taken out, dried at 80 to 140° C., and calcinated. The calcination may be performed by increasing the temperature at a temperature increasing rate of 0.1° C. to 10° C./min if necessary, followed by a heat treatment at 450° C. to 700° C. for 2 to 10 hours. By the calcinating, the structure directing agent in the pores is removed to form pores that act as a molecular sieve in the core and the silicate film.

(Ion-Exchange Treatment of Silicate-Coated MFI-Type Zeolite)

When a mineralizer is used in preparation of the MFI-type zeolite to form a core, it is preferable that the silicate-coated MFI-type zeolite be subjected to an ion-exchange treatment after the calcination, to obtain the silicate-coated MFI-type zeolite of the present invention. The ion-exchange treatment method is the same as that in the above description ([0049]). However, when an ion-exchange treatment is performed before a silicate-coating treatment, an ion-exchange treatment after coating with a silicate may not be performed.

Therefore, when a mineralizer is used in preparation of the MFI-type zeolite to form a core, an ion-exchange treatment may be performed during the preparation of the MFI-type zeolite to form a core or after the calcination of the silica-coated MFI-type zeolite.

Hereinafter, the method of producing the silicate-coated MFI-type zeolite of the present invention will be described with reference to FIG. 1. FIG. 1 is one example of a process of producing the silicate-coated MFI-type zeolite of the present invention.

As shown in FIG. 1, in order to first synthesize the MFI-type zeolite to form a core in a process of producing the silicate-coated MFI-type zeolite of the present invention, a precursor liquid is prepared (step S101), and an MFI-type zeolite is formed by a hydrothermal synthesis treatment (step S102) and dried (step S103). The MFI-type zeolite to form a core may be prepared by the method described above, or a commercially available product may be used as long as the peak area ratio b/a is 1 or more.

Subsequently, the MFI-type zeolite is immersed in a precursor liquid for formation of a silicate film in which predetermined amounts of a silica source and a structure directing agent are dispersed ii water or an aqueous alcohol solution (step S104). It is preferable that the MFI-type zeolite before immersion in the precursor liquid for formation of a silicate film be not calcinated after the hydrothermal synthesis treatment of S102, that is, have no calcinating history. This is because in an MFI-type zeolite that has not been calcinated, a silicate film is likely to uniformly grow.

After that, the MFI-type zeolite immersed in the precursor liquid for formation of a silicate film is hydrothermally synthesized at a predetermined temperature to form a silicate film (step S105). The hydrothermal synthesis treatment is performed at a temperature range of 100 to 250° C. for 0.5 to 48 hours.

After the hydrothermal synthesis treatment, the silicate-coated MFI-type zeolite is dried (step S106), and calcinated at a temperature range of 450° C. to 700° C. for a predetermined time (step S107). By the calcination, pores that act as a molecular sieve are formed in the core and the silicate film to produce a silicate-coated MFI-type zeolite.

The silicate-coated MFI-type zeolite prepared by the above-described method is not colored by a Hammett indicator (p-dimethylaminoazobenzene) with a pKa value of +3.3, that is, the pKa value is +3.3 or more and an acid site on the outer surface of the MFI-type zeolite is coated with a silicate inert to a reaction. When the silicate-coated MFI-type zeolite prepared by the above-described method is used in a disproportionation reaction or an alkylation reaction of an aromatic hydrocarbon, especially toluene, p-xylene can be produced at a high selectivity.

When the MFI-type zeolite to form a core is hydrothermally synthesized using an MFI-type zeolite precursor liquid containing a mineralizer in the steps S101 and S102, it is preferable that the drying process of step S103 be performed followed by calcinating and an ion-exchange treatment, or the calcinating process of step S107 be performed followed by an ion-exchange treatment.

<Disproportionation Reaction of Aromatic Hydrocarbon>

Production of p-xylene by a disproportionation reaction of an aromatic hydrocarbon using the silicate-coated MFI-type zeolite according to the embodiment of the present invention will be described.

It is preferable that a starting material for production of p-xylene be toluene. Toluene as the starting material may contain water, an olefin, a sulfur compound, and a nitrogen compound as impurities. It is preferable that the content of the impurities be smaller. The content of water is preferably 200 ppm by mass or less, and more preferably 100 ppm by mass or less. The content of olefin is preferably 1% by mass or less, and more preferably 0.5% by mass or less. The content of nitrogen compound is preferably 1 ppm by mass or less.

Herein, the content of water is a value measured by Karl Fischer coulometric titration in JIS K 2275 "Crude oil and petroleum product—Determination of water content," the content of olefin is a value measured by a fluorescence indicator absorption method in JIS K 2536 "Petroleum products—Component test method," and the content of nitrogen compound is a value measured by a chemiluminescence method in JIS K 2609 "Crude petroleum and petroleum products—Determination of nitrogen content."

In the disproportionation reaction of an aromatic hydrocarbon, it is preferable that the aromatic hydrocarbon be supplied at a range of liquid hourly space velocity (LHSV) of 0.01 h$^{-1}$ to 10 h$^{-1}$, to be brought into contact with the silicate-coated MFI-type zeolite according to the embodiment. The aromatic hydrocarbon is supplied further preferably at a range of liquid hourly space velocity (LHSV) of 0.1 h$^{-1}$ to 5 h$^{-1}$.

In the disproportionation reaction of an aromatic hydrocarbon, it is preferable that the reaction be performed by heating at a range of 200° C. to 550° C. When the reaction temperature is lower than 200° C., the reaction is unlikely to proceed, and when the reaction temperature is higher than 550° C., the selectivity of p-xylene decreases, or energy consumption increases. Therefore, This is not preferable. The reaction temperature is more preferably 230° C. to 530° C., and particularly preferably 260° C. to 510° C. The pressure during the reaction is preferably atmospheric pressure to 10 MPaG, and more preferably 0.5 MPaG to 5 MPaG.

<Alkylation Reaction of Aromatic Hydrocarbon>

Production of p-xylene by an alkylation reaction of an aromatic hydrocarbon using the silicate-coated MFI-type zeolite according to the embodiment of the present invention will be described.

Examples of an aromatic hydrocarbon as a starting material may include benzene and toluene. The aromatic hydrocarbon as a starting material may contain a hydrocarbon compound other than benzene and toluene. However, a starting material containing m-xylene or o-xylene is not preferable since a target product is p-xylene. The starting material is more preferably toluene having high reactivity.

Examples of an alkylating agent used in the alkylation reaction of an aromatic hydrocarbon may include methanol and dimethyl ether. They may be commercially available products, but methanol or dimethyl ether produced from synthetic gas such as mixed gas of hydrogen and carbon monoxide, or dimethyl ether produced by a dehydration reaction of methanol may be used as a starting material. Examples of impurities that may be present in benzene, toluene, and dimethyl ether may include water, an olefin, a sulfur compound, and a nitrogen compound, but it is preferable that the amounts thereof be smaller. The content of water is 200 ppm by weight or less, and more preferably 100 ppm by weight or less. The content of olefin is 1% by weight or less, and more preferably 0.5% by weight or less. The contents of sulfur compound and the content of nitrogen compound are each 1 ppm by weight or less, and more preferably 0.1 ppm by weight or less.

Herein, the content of water is a value measured by Karl Fischer coulometric titration in JIS K 2275 "Crude oil and petroleum product—Determination of water content," the content of olefin is a value measured by a fluorescence indicator absorption method in JIS K 2536 "Petroleum products—Component test method," the content of sulfur compound is a value measured by JIS K 2541 "Crude oil and petroleum products-Determination of sulfur content," and the content of nitrogen compound is a value measured by a chemiluminescence method in JIS K 2609 "Crude petroleum and petroleum products—Determination of nitrogen content."

The ratio of the alkylating agent to the aromatic hydrocarbon in the alkylation reaction of the aromatic hydrocarbon is preferably 5/1 to 1/20, more preferably 2/1 to 1/10, and particularly preferably 1/1 to 1/5 as a ratio by mole of a methyl group to the aromatic hydrocarbon. When the ratio of the alkylating agent to the aromatic hydrocarbon is extremely large, an undesirable reaction between alkylating agents proceeds, and coking may be caused to deteriorate the catalyst. Therefore, This is not preferable. In contrast, when the ratio of the alkylating agent to the aromatic hydrocarbon is extremely small, the alkylation reaction of an aromatic hydrocarbon does not proceed, and recycle of the aromatic hydrocarbon increases. Therefore, This is not preferable.

It is desirable that the alkylation reaction of an aromatic hydrocarbon be performed by supplying the aromatic hydrocarbon as a starting material at a liquid hourly space velocity (LHSV) of $0.01\ h^{-1}$ or more, and more preferably $0.1\ h^{-1}$ or more and $10\ h^{-1}$ or less, and more preferably $5\ h^{-1}$ or less to be brought into contact with the silicate-coated MFI-type zeolite according to the embodiment.

Reaction conditions of the alkylation reaction are not particularly limited, but the reaction temperature is preferably 200° C. or higher, more preferably 230° C. or higher, and particularly preferably 260° C. or higher, and preferably 550° C. or lower, more preferably 530° C. or lower, and particularly preferably 510° C. or lower. The pressure is preferably equal to or more than atmospheric pressure, more preferably 0.1 MPaG or more, and particularly preferably 0.5 MPaG or more, and preferably 10 MPaG or less, and more preferably 5 MPaG or less.

In the alkylation reaction, an inert gas such as nitrogen and helium or hydrogen for suppressing coking may be circulated and at this time, the pressure may be atmospheric pressure or be pressurized. Further, when the reaction temperature is too low, the activation of the aromatic hydrocarbon or the alkylating agent is insufficient. Therefore, the conversion ratio of the aromatic hydrocarbon as a starting material is low. In contrast, when the reaction temperature is too high, a lot of energy is consumed, and the catalyst life tends to shorten.

The silicate-coated MFI-type zeolite according to the present invention is characterized in that the peak area ratio b/a of the peak b at $2\theta=8.4$ to $9.7°$ to the peak a at $2\theta=7.0$ to $8.4°$ in an X-ray diffraction spectrum, is 1 or more, and the pKa value measured by a Hammett indicator is +3.3 or more. The silicate-coated MFI-type zeolite of the present invention is used in the disproportionation reaction or the alkylation reaction of an aromatic hydrocarbon, especially toluene, high purity p-xylene can be produced at a high selectivity.

EXAMPLES

Hereinafter, the present invention will be described in more detail using the following Examples. The present invention is not limited to Examples described below.
<Preparation of Silicate-Coated MFI-Type Zeolite>

ZSM-5 having a peak area ratio b'/a' of 1 or more (Synthesis Examples 1 to 5 and 7), and ZSM-5 having a peak area ratio b'/a' of less than 1 (Synthesis Example 6 and commercially available product) were first produced or prepared. Each of the ZSM-5 of Synthesis Examples 1 to 7 and the commercially available product was coated with a silicate to prepare a silicate-coated MFI-type zeolite (Examples 1 to 5 and Comparative Examples 1 to 3).

Synthesis Example 1

Tetraethyl orthosilicate (TEOS), aluminum nitrate, sodium hydroxide, tetrapropylammonium bromide (TPABr), and deionized water were used at $SiO_2:Al_2O_3:Na_2O:TPABr:H_2O=1:0.01:0.1:0.2:42$ (ratio by mole; ratios by mole of a silica source, an alumina source, and a sodium source were those in terms of oxide), and hydrothermally synthesized at 180° C. for 24 hours. After the hydrothermal synthesis, the resultant product was washed using ion-exchanged water at 25° C. and filtered, and dried at 130° C. The $SiO_2/Al_2O_3$ ratio of the obtained ZSM-5 was 97 (ratio by mole).

Synthesis Example 2

Fumed silica, aluminum hydroxide, tetrapropylammonium bromide, ammonium fluoride, and deionized water were used at $SiO_2:Al_2O_3:TPABr:F^-:H_2O=1:0.025:0.125:0.9:33$ (ratio by mole; ratios by mole of a silica source and an alumina source were those in terms of oxide), and hydrothermally synthesized at 180° C. for 70 hours. After the hydrothermal synthesis, the resultant product was washed using ion-exchanged water at 25° C. and filtered, dried at 130° C. for 12 hours, calcinated at 550° C. for 7 hours, subjected to ion exchange, dried at 130° C. for 12 hours, and calcinated at 450° C. for 2 hours. The $SiO_2/Al_2O_3$ ratio of the obtained ZSM-5 was 69 (ratio by mole). The content of fluorine of the obtained ZSM-5 was measured by an X-ray photoelectron spectroscopy to be less than 0.1% by mole. This shows that the ZSM-5 does not contain fluorine.

Synthesis Example 3

Tetraethyl orthosilicate (TEOS), aluminum nitrate, sodium hydroxide, tetrapropylammonium bromide, ammonium fluoride, and deionized water were used at $SiO_2:Al_2O_3:Na_2O:TPABr:F^-:H_2O=1:0.01:0.1:0.2:1.4:42$ (ratio by mole; ratios by mole of a silica source, an alumina source, and a sodium source were those in terms of oxide), and hydrothermally synthesized at 180° C. for 70 hours. After the hydrothermal synthesis, the resultant product was washed using ion-exchanged water at 25° C. and filtered, dried, calcinated at 550° C. for 7 hours, subjected to ion exchange, dried at 130° C. for 12 hours, and calcinated at 450° C. for 2 hours. The $SiO_2/Al_2O_3$ ratio of the obtained ZSM-5 was 97 (ratio by mole).

Synthesis Example 4

Fumed silica, aluminum hydroxide, tetrapropylammonium bromide, ammonium fluoride, and deionized water were used at $SiO_2:Al_2O_3:TPABr:F^-:H_2O=1:0.042:0.125:0.9:33$ (ratio by mole; ratios by mole of a silica source and an alumina source were those in terms of oxide), and hydrothermally synthesized at 180° C. for 70 hours. After the hydrothermal synthesis, the resultant product was washed with water and filtered, dried at 130° C. for 12 hours, calcinated at 550° C. for 7 hours, subjected to ion exchange, dried at 130° C. for 12 hours, and calcinated at 450° C. for 2 hours. The $SiO_2/Al_2O_3$ ratio of the obtained ZSM-5 was 60

(ratio by mole), and the proportion of aluminum in sites other than a skeleton in all aluminum was 0%.

Synthesis Example 5

The ZSM-5 obtained in Synthesis Example 4 was classified using a 635-mesh (20 μm) sieve, to obtain fine ZSM-5.

Synthesis Example 6

The ZSM-5 obtained in Synthesis Example 1 was calcinated at 550° C. for 2 hours, subjected to ion exchange, dried at 130° C. for 12 hours, and calcinated at 450° C. for 2 hours. The $SiO_2/Al_2O_3$ ratio was 97 (ratio by mole) that was the same as in Synthesis Example 1.

Synthesis Example 7

The same composition as in Synthesis Example 4 was subjected to a hydrothermal synthesis treatment at 180° C. for 70 hours through the same process as in Synthesis Example 4, calcinated at 550° C. for 7 hours. A product obtained without an ion-exchange treatment was washed using ion-exchanged water at 25° C. and filtered, dried at 130° C. for 12 hours, and calcinated at 550° C. for 7 hours. The $SiO_2/Al_2O_3$ ratio of the obtained ZSM-5 was 42 (ratio by mole), and the proportion of aluminum in sites other than a skeleton in all aluminum was 42%.

(Commercially Available ZSM-5)

The commercially available ZSM-5 was used. The $SiO_2/Al_2O_3$ ratio thereof was 49 (ratio by mole).

Example 1

Tetraethyl orthosilicate (TEOS), tetrapropylammonium hydroxide (TPAOH), ethanol (EtOH), and deionized water were used to prepare a precursor liquid for formation of a silicate film so that $SiO_2$:TPAOH:EtOH:$H_2O$ was 2:0.05:0.8:120 (ratio by mole). The ZSM-5 obtained in Synthesis Example 1 and the prepared precursor liquid for formation of a silicate film were mixed and hydrothermally synthesized at 180° C. for 24 hours. After the hydrothermal synthesis, the resultant product was washed using ion-exchanged water at 25° C. and filtered, dried at 130° C. for 12 hours, calcinated at 550° C. for 5 hours, subjected to ion exchange, dried at 130° C. for 12 hours, and calcinated at 550° C. for 2 hours to obtain a silicate-coated MFI-type zeolite. The pKa value of the resulting silicate-coated MFI-type zeolite was +3.3 or more, that is, the color of a Hammett indicator having a pKa of +3.3 was not changed.

Example 2

Tetraethyl orthosilicate (TEOS), tetrapropylammonium hydroxide (TPAOH), ethanol (EtOH), and deionized water were used to prepare a precursor liquid for formation of a silicate film so that $SiO_2$:TPAOH:EtOH:$H_2O$ was 2:0.05:0.8:120 (ratio by mole). The ZSM-5 obtained in Synthesis Example 2 and the prepared precursor liquid for formation of a silicate film were mixed and hydrothermally synthesized at 180° C. for 24 hours. After the hydrothermal synthesis, the resultant product was washed using ion-exchanged water at 25° C. and filtered, dried at 130° C. for 12 hours, and calcinated at 550° C. for 5 hours to obtain a silicate-coated MFI-type zeolite. The pKa value of the resulting silicate-coated MFI-type zeolite was +3.3 or more, that is, the color of a Hammett indicator having a pKa of +3.3 was not changed.

Example 3

Tetraethyl orthosilicate (TEOS), tetrapropylammonium hydroxide (TPAOH), ethanol (EtOH), and deionized water were used to prepare a precursor liquid for formation of a silicate film so that $SiO_2$:TPAOH:EtOH:$H_2O$ was 2:0.05:0.8:120 (ratio by mole). The ZSM-5 obtained in Synthesis Example 3 and the prepared precursor liquid for formation of a silicate film were mixed and hydrothermally synthesized at 180° C. for 24 hours. After the hydrothermal synthesis, the resultant product was washed using ion-exchanged water at 25° C. and filtered, dried, calcinated at 550° C. for 5 hours, subjected to ion exchange, dried at 130° C. for 12 hours, and calcinated at 550° C. for 5 hours to obtain a silicate-coated MFI-type zeolite. The pKa value of the resulting silicate-coated MFI-type zeolite was +3.3 or more, that is, the color of a Hammett indicator having a pKa of +3.3 was not changed.

Example 4

Tetraethyl orthosilicate (TEOS), tetrapropylammonium hydroxide (TPAOH), ethanol (EtOH), and deionized water were used to prepare a precursor liquid for formation of a silicate film so that $SiO_2$:TPAOH:EtOH:$H_2O$ was 2:0.05:0.8:120 (ratio by mole). The ZSM-5 obtained in Synthesis Example 4 and the prepared precursor liquid for formation of a silicate film were mixed and hydrothermally synthesized at 180° C. for 24 hours. After the hydrothermal synthesis, the resultant product was washed using ion-exchanged water at 25° C. and filtered, dried at 130° C. for 12 hours, and calcinated at 550° C. for 5 hours to obtain a silicate-coated MFI-type zeolite. The pKa value of the resulting silicate-coated MFI-type zeolite was +3.3 or more, that is, the color of a Hammett indicator having a pKa of +3.3 was not changed.

Example 5

Tetraethyl orthosilicate (TEOS), tetrapropylammonium hydroxide (TPAOH), ethanol (EtOH), and deionized water were used to prepare a precursor liquid for formation of a silicate film so that $SiO_2$:TPAOH:EtOH:$H_2O$ was 2:0.05:0.8:120 (ratio by mole). The ZSM-5 obtained in Synthesis Example 5 and the prepared precursor liquid for formation of a silicate film were mixed and hydrothermally synthesized at 180° C. for 24 hours. After the hydrothermal synthesis, the resultant product was washed using ion-exchanged water at 25° C. and filtered, dried at 130° C. for 12 hours, and calcinated at 550° C. for 5 hours to obtain a silicate-coated MFI-type zeolite. The pKa value of the resulting silicate-coated MFI-type zeolite was +3.3 or more, that is, the color of a Hammett indicator having a pKa of +3.3 was not changed.

Comparative Example 1

Tetraethyl orthosilicate (TEOS), tetrapropylammonium hydroxide (TPAOH), ethanol (EtOH), and deionized water were used to prepare a precursor liquid for formation of a silicate film so that $SiO_2$:TPAOH:EtOH:$H_2O$ was 2:0.05:0.8:120 (ratio by mole). The ZSM-5 obtained in Synthesis Example 6 and the prepared precursor liquid for formation of a silicate film were mixed and hydrothermally synthesized at 180° C. for 24 hours. After the hydrothermal synthesis, the resultant product was washed using ion-exchanged water at 25° C. and filtered, dried at 130° C. for 12 hours, and calcinated at 550° C. for 5 hours to obtain a silicate-coated MFI-type zeolite. The pKa value of the resulting silicate-coated MFI-type zeolite was −3.0 or more and +1.5 or less, that is, the color of a Hammett indicator having a pKa of +1.5 was changed, and the color of a Hammett indicator having a pKa of −3.0 was not changed.

Comparative Example 2

Tetraethyl orthosilicate (TEOS), tetrapropylammonium hydroxide (TPAOH), ethanol (EtOH), and deionized water were used to prepare a precursor liquid for formation of a silicate film so that $SiO_2$:TPAOH:EtOH:$H_2O$ was 2:0.05: 0.8:120 (ratio by mole). The commercially available ZSM-5 and the prepared precursor liquid for formation of a silicate film were mixed and hydrothermally synthesized at 180° C. for 24 hours. After the hydrothermal synthesis, the resultant product was washed using ion-exchanged water at 25° C. and filtered, dried at 130° C. for 12 hours, and calcinated at 550° C. for 5 hours to obtain a silicate-coated MFI-type zeolite. The pKa value of the resulting silicate-coated MFI-type zeolite was −5.6 or more and −3.0 or less, that is, the color of a Hammett indicator having a pKa of −3.0 was changed, and the color of a Hammett indicator having a pKa of −5.6 was not changed.

Comparative Example 3

Tetraethyl orthosilicate (TEOS), tetrapropylammonium hydroxide (TPAOH), ethanol (EtOH), and deionized water were used to prepare a precursor liquid for formation of a silicate film so that $SiO_2$:TPAOH:EtOH:$H_2O$ was 2:0.05: 0.8:120 (ratio by mole). The ZSM-5 obtained in Synthesis Example 7 and the prepared precursor liquid for formation of a silicate film were mixed and hydrothermally synthesized at 180° C. for 24 hours. After the hydrothermal synthesis, the resultant product was washed using ion-exchanged water at 25° C. and filtered, dried at 130° C. for 12 hours, and calcinated at 550° C. for 5 hours to obtain a silicate-coated MFI-type zeolite. The pKa value of the resulting silicate-coated MFI-type zeolite was −3.0 or more and +1.5 or less, that is, the color of a Hammett indicator having a pKa of +1.5 was changed, and the color of a Hammett indicator having a pKa of −3.0 was not changed.

<Catalyst Characteristics>

Figure 7:
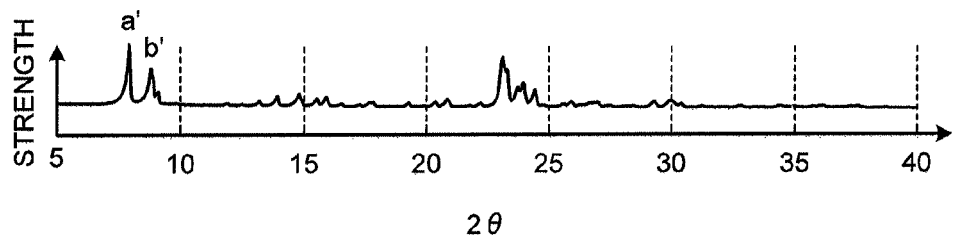
FIG. 7 is an X-ray diffraction chart of a ZSM-5 type zeolite according to Synthesis Example 6.
Figure 8:
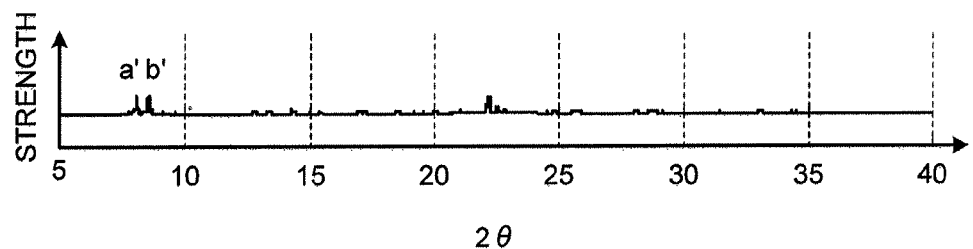
FIG. 8 is an X-ray diffraction chart of a ZSM-5 type zeolite according to Synthesis Example 7.
Figure 9:
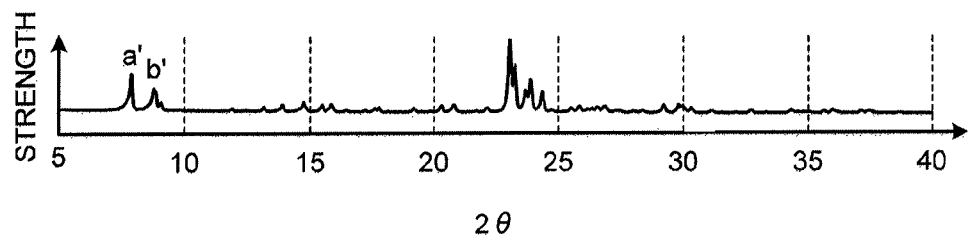
FIG. 9 is an X-ray diffraction chart of a commercially available ZSM-5 type zeolite.
Figure 10:
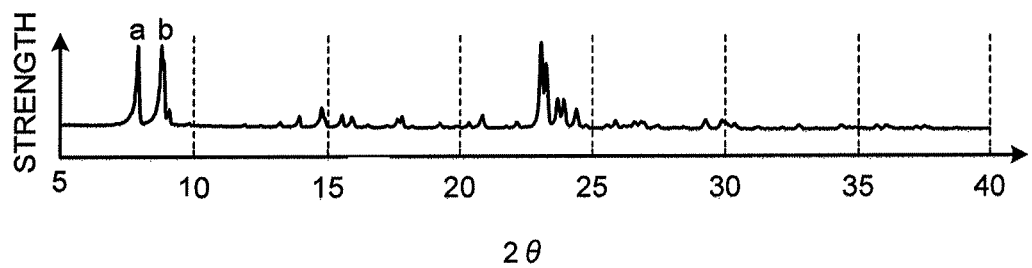
FIG. 10 is an X-ray diffraction chart of a silicate-coated ZSM-5 type zeolite according to Example 1.
Figure 11:
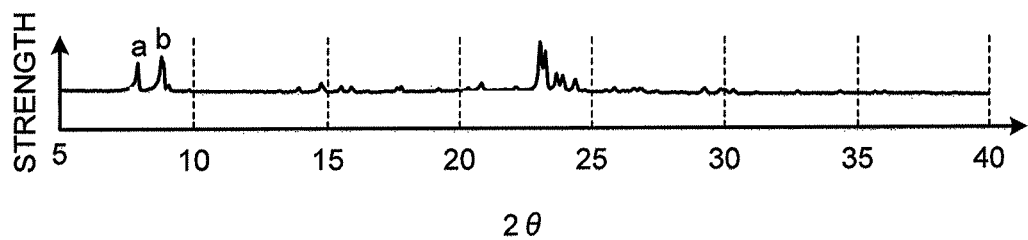
FIG. 11 is an X-ray diffraction chart of a silicate-coated ZSM-5 type zeolite according to Example 2.
Figure 12:
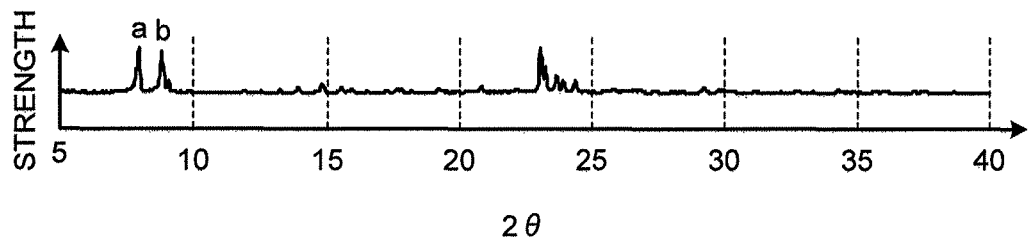
FIG. 12 is an X-ray diffraction chart of a silicate-coated ZSM-5 type zeolite according to Example 3.
Figure 13:
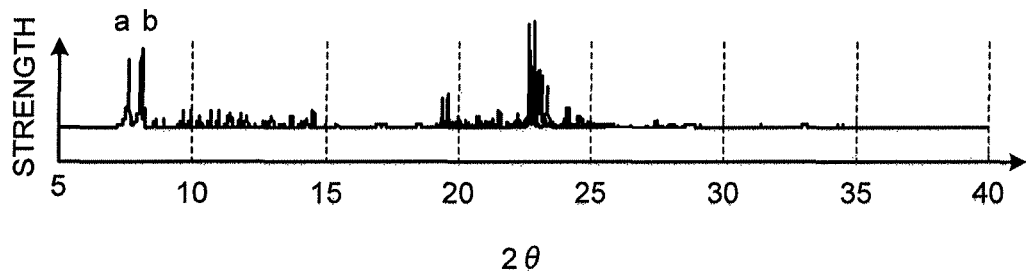
FIG. 13 is an X-ray diffraction chart of a silicate-coated ZSM-5 type zeolite according to Example 4.
Figure 14:
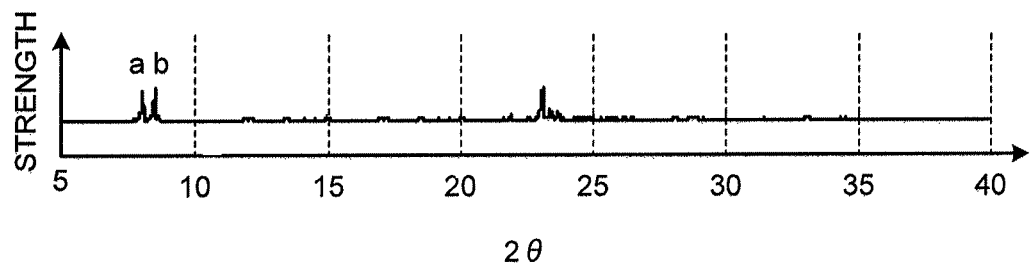
FIG. 14 is an X-ray diffraction chart of a silicate-coated ZSM-5 type zeolite according to Example 5.
Figure 15:
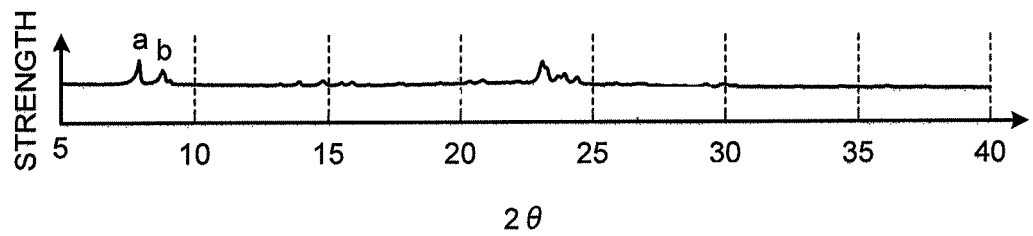
FIG. 15 is an X-ray diffraction chart of a silicate-coated ZSM-5 type zeolite according to Comparative Example 1.
Figure 16:
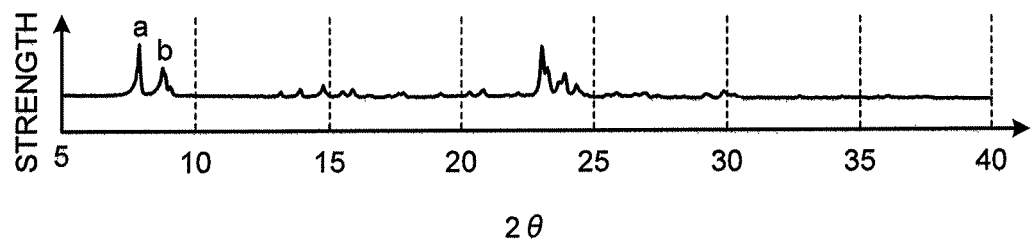
FIG. 16 is an X-ray diffraction chart of a silicate-coated ZSM-5 type zeolite according to Comparative Example 2.
Figure 17:
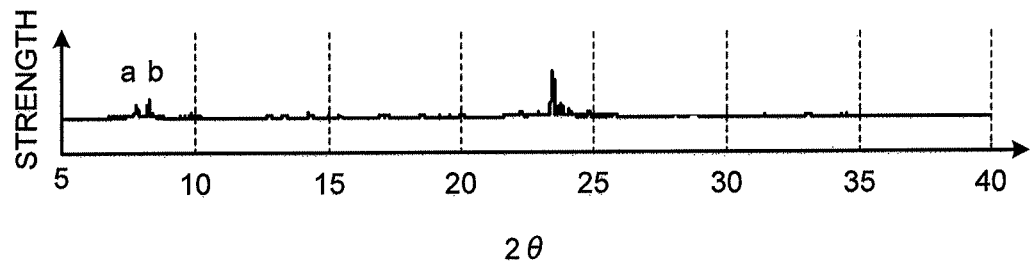
FIG. 17 is an X-ray diffraction chart of a silicate-coated ZSM-5 type zeolite according to Comparative Example 3.

The crystal structure of each of the catalysts of Synthesis Examples 1 to 7, Examples 1 to 5, and Comparative Examples 1 to 3, and the commercially available ZSM-5, which were obtained as described above, was analyzed by X-ray. X-ray diffraction charts of the ZSM-5-type zeolite catalysts according to Synthesis Examples 1 to 7 are shown in FIGS. 2 to 8, respectively. An x-ray diffraction chart of the commercially available ZSM-5 is shown in FIG. 9. X-ray diffraction charts of the ZSM-5-type zeolite catalysts according to Examples 1 to 5 are shown in FIGS. 10 to 14, respectively. X-ray diffraction charts of the ZSM-5-type zeolite catalysts according to Comparative Examples 1 to 3 are shown in FIGS. 15 to 17, respectively.

Analysis conditions used to obtain an X-ray diffraction spectrum are as follows.

Device: Ultima IV manufactured by Rigaku Corporation
X-ray source: CuKα1
Tube power: 30 kV
Tube current: 20 mA
Scan rate: 4°/min
Step width: 0.02°

In Examples 1 to 5 and Comparative Examples 1 to 3, the crystallinities, the crystallite diameters, the area of peak a at 7.0 to 8.4° in the X-ray diffraction spectrum, the area of peak b at 8.4 to 9.7° in the X-ray diffraction spectrum, and the peak area ratio b/a were determined from the obtained X-ray diffraction charts. In Synthesis Examples 1 to 7 and the commercially available ZSM-5, the crystallinities, the crystallite diameters, the area of peak a' at 7.0 to 8.4° in the X-ray diffraction spectrum, the area of peak b' at 8.4 to 9.7° in the X-ray diffraction spectrum, and the peak area ratio b'/a' were determined. In Synthesis Examples, Examples, and Comparative Examples, the proportion of aluminum in a skeleton (Al in a skeleton) and the $SiO_2/Al_2O_3$ ratio in the skeleton were determined by $^{29}$Al-NMR, and the particle diameter was measured with a laser diffraction particle size distribution measurer. The results are shown in Table 2.

In the present application, aluminum in the skeleton represents four-coordinated aluminum measured by $^{29}$Al-NMR, and aluminum in sites other than the skeleton represents six-coordinated aluminum measured by $^{29}$Al-NMR. Therefore, the proportion of aluminum in the skeleton represents the proportion of the four-coordinated aluminum in the sum of the four-coordinated and the six-coordinated aluminum calculated from $^{29}$Al-NMR spectrum. The particle diameter is a model diameter in a particle size distribution on the basis of volume.

The crystallinity is calculated from the ratio of the strength of a (101) plane of ZSM-5 ($SiO_2/Al_2O_3$=30) available from N. E. CHEMCAT Corporation after calcinating at 600° C. for 5 hours to the strength of a (101) plane of each zeolite (calculation expression is as follows). The crystallite diameter is a value of the (101) plane.

Crystallinity (%)=(strength of (101) plane of each zeolite)/(strength of (101) plane of ZSM-5 available from N. E. CHEMCAT Corporation)× 100

TABLE 2

| | Crystallinity (%) | Crystallite diameter (nm) | Peak a (Peak a') area | Peak b (Peak b') area | Peak area ratio b/a (b'/a') | Proportion of Al in skeleton (%) | $SiO_2/Al_2O_3$ in skeleton | Particle diameter (μm) | Increased amount after coating (%) | pKa |
|---|---|---|---|---|---|---|---|---|---|---|
| Synthesis Example 1 | 67.2 | 107.9 | 112098 | 255766 | 2.3 | 100 | 97 | 26.8 | — | |
| Example 1 | 83.9 | 110.8 | 163231 | 227331 | 1.4 | 100 | 110 | 27.7 | 12 | +3.3 or more |
| Synthesis Example 2 | 34.7 | 107.5 | 55879 | 538362 | 9.6 | 100 | 69 | 30.9 | — | |

TABLE 2-continued

| | Crystallinity (%) | Crystallite diameter (nm) | Peak a (Peak a') area | Peak b (Peak b') area | Peak area ratio b/a (b'/a') | Proportion of Al in skeleton (%) | SiO$_2$/Al$_2$O$_3$ in skeleton | Particle diameter (μm) | Increased amount after coating (%) | pKa |
|---|---|---|---|---|---|---|---|---|---|---|
| Example 2 | 27.9 | 111.8 | 54332 | 103882 | 1.9 | 100 | 112 | 35.1 | 61 | +3.3 or more |
| Synthesis Example 3 | 78.9 | 114.4 | 122707 | 166248 | 1.4 | 100 | 97 | 35.5 | — | |
| Example 3 | 43.9 | 72.7 | 111374 | 138365 | 1.2 | 100 | 126 | 37.1 | 30 | +3.3 or more |
| Synthesis Example 4 | 117.0 | 90.7 | 69460 | 96100 | 1.4 | 100 | 60 | 37.0 | — | |
| Example 4 | 88.5 | 72.8 | 46406 | 52798 | 1.1 | 100 | 64 | 38.5 | 1 | +3.3 or more |
| Synthesis Example 5 | 120 | 68.8 | 204433 | 253885 | 1.2 | 100 | 64 | 22.0 | — | |
| Example 5 | 117 | 82.6 | 68526 | 92999 | 1.4 | 100 | 82 | 23.5 | 19 | +3.3 or more |
| Synthesis Example 6 | 88.0 | 63.3 | 171341 | 140125 | 0.8 | 100 | 97 | 26.8 | — | |
| Comparative Example 1 | 72.6 | 60.3 | 111162 | 89513 | 0.8 | 100 | 146 | 31.0 | 51 | −3.0 to +1.5 |
| Commercially Available ZSM-5 | 52.4 | 80.8 | 94127 | 83504 | 0.9 | 100 | 49 | 27.0 | — | |
| Comparative Example 2 | 74.7 | 72.0 | 130167 | 111627 | 0.9 | 100 | 75 | 32.1 | 54 | −5.6 to −3.0 |
| Synthesis Example 7 | 52.9 | 83.1 | 31433 | 54563 | 1.7 | 58 | 72 | 38.0 | | |
| Comparative Example 3 | 95.2 | 81.5 | 42745 | 54590 | 1.3 | 92 | 78 | 39.0 | 12 | −3.0 to +1.5 |

As shown in FIGS. 2 to 6 and Table 2, it can be seen that the peak area ratios b'/a' of the peak area b' at 8.4 to 9.7° to the peak area a' at 7.0 to 8.4° in the X-ray diffraction charts in Synthesis Examples 1 to 5 are 1 or more (2.3, 9.6, 1.4, 1.4, and 1.2). In contrast, as shown in FIGS. 7 and 9, the peak area ratios b'/a' in Synthesis Example 6 and the commercially available ZSM-5 are 0.8 and 0.9, respectively, which are smaller than 1. It is clearly seen that a developed crystal plane of ZSM-5 is different from those in Synthesis Examples 1 to 5. As shown in FIG. 8 and Table 2, in Synthesis Example 7 in which washing with water is performed without ion exchange after the calcination, the peak area ratio b'/a' is 1 or more, but the proportion of aluminum in the skeleton is small (58%), that is, it can be seen that the proportion of aluminum in sites other than the skeleton is large (42%).

As shown in FIGS. 10 to 14 and Table 2, it can be seen that in Examples 1 to 5, the peak area ratios b/a of the peak area b at 8.4 to 9.7° to the peak area a at 7.0 to 8.4° in the X-ray diffraction charts are 1 or more (1.4, 1.9, 1.2, 1.1, and 1.4), and the pKa values are +3.3 or more. In contrast, as shown in FIGS. 15 and 16, the peak area ratios b/a in Comparative Examples 1 and 2 are 0.8 and 0.9, respectively, which are smaller than 1. It is clearly seen that a developed crystal plane of silicate-coated ZSM-5 is different from those in Examples 1 to 5. As shown in FIG. 17 and Table 2, in Comparative Example 3, it can be seen that the peak area ratio b/a is 1 or more, and the pKa value is −3.0 to +1.5. In Comparative Example 3 in which washing with water is performed without the ion-exchange treatment, the population of aluminum in the skeleton is not 100% (92%), that is, it can be seen that aluminum in sites other than the skeleton (8%) is present.

<Catalytic Performance Evaluation Test 1>

In the presence of each of the MFI-type zeolites in Synthesis Examples 1 to 3, and 6, the commercially available ZSM-5, and the silicate-coated MFI-type zeolites in Examples 1 to 3 and Comparative Examples 1 and 2, a disproportionation reaction of toluene was performed, and the conversion ratio of toluene and the selectivity of p-xylene were measured.

A fixed bed reactor was charged with 20 mg of the MFI-type zeolite or the silicate-coated MFI-type zeolite. A disproportionation reaction was performed at 400° C., 0.9 MPaG, and a LHSV of 0.48 h$^{-1}$ under a hydrogen/toluene ratio of 60 mol/mol. A product in an outlet of the reactor was analyzed by gas chromatography to determine the conversion ratio of toluene and the selectivity of p-xylene.

Measurement device: GC-2014 made by Shimadzu Corporation Column: capillary column Xylene Master, inner diameter: 0.32 mm, length: 50 m Temperature condition: column initial temperature: 50° C., temperature increasing rate: 2° C./min, temperature of detector (FID): 250° C.

Carrier gas: helium

The conversion ratio of toluene and the selectivity of p-xylene were calculated by the following equation.

Conversion ratio of toluene (% by mole)=100−(unreacted toluene (mol)/starting material toluene (mol)))×100

Selectivity of p-xylene (% by mole)=100 (produced p-xylene (mol)/produced C8 aromatic hydrocarbon (mol))×100

The results in the catalytic performance evaluation test and the pKa value are shown in Table 3 below.

TABLE 3

| | Toluene disproportional performance | | |
|---|---|---|---|
| | Toluene conversion ratio (%) | p-Xylene selectivity (%) | pKa |
| Synthesis Example 1 | 4.5 | 32.3 | — |
| Example 1 | 4.6 | 91.6 | +3.3 or more |
| Synthesis Example 2 | 4.8 | 49.3 | — |
| Example 2 | 4.0 | 98.5 | +3.3 or more |
| Synthesis Example 3 | 6.2 | 34.9 | — |
| Example 3 | 5.2 | 85.1 | +3.3 or more |
| Synthesis Example 6 | 4.5 | 32.3 | — |
| Comparative Example 1 | 2.6 | 65.6 | −3.0 to +1.5 |
| Commercially Available ZSM-5 | 15.0 | 25.6 | — |
| Comparative Example 2 | 10.7 | 51.2 | −5.6 to −3.0 |

As shown in Table 3, it can be seen that in Examples 1 to 3 using the silicate-coated MFI-type zeolite according to the present invention, while the conversion ratio in Synthesis Examples 1 to 3 that are before being coated with a silicate is held (about 4 to 5%), the selectivity of p-xylene can be largely improved.

In contrast, in Comparative Examples 1 and 2 using silicate-coated MFI-type zeolites that do not satisfy the present invention, it can be seen that the conversion ratio is inferior to those in Synthesis Example 6 and the commercially available ZSM-5 that are before being coated with a silicate, and at the same time, the selectivity of p-xylene cannot be improved.

<Catalytic Performance Evaluation Test 2>

In the presence of each of the silicate-coated MFI-type zeolites in Examples 2, 4, and 5 and Comparative Example 3, a disproportionation reaction of toluene was performed, and the conversion ratio of toluene and the selectivity of p-xylene were measured.

A fixed bed reactor was charged with 0.5 g of the silicate-coated MFI-type zeolite. A disproportionation reaction was performed at 500° C., normal pressure, and a LHSV of 6.0 h$^{-1}$ under a hydrogen/toluene ratio of 1.0 mol/mol. A product in an outlet of the reactor was analyzed by gas chromatography to determine the conversion ratio of toluene and the selectivity of p-xylene.

TABLE 4

| | Toluene disproportional performance | | |
|---|---|---|---|
| | Toluene conversion ratio (%) | p-Xylene selectivity (%) | pKa |
| Example 2 | 6.6 | 98.5 | +3.3 or more |
| Example 4 | 9.6 | 98.8 | +3.3 or more |
| Comparative Example 3 | 9.5 | 79.3 | −3.0 to +1.5 |
| Example 5 | 11.9 | 97.9 | +3.3 or more |

As shown in Table 4, it can be seen that the selectivity of p-xylene in Example 4 using as a catalyst the silicate-coated MFI-type zeolite in which ion-exchange treatment was performed before being coated with a silicate and the proportion of aluminum in sites other than the skeleton is 0% is higher than that in Comparative Example 3 using as a catalyst the silicate-coated MFI zeolite in which washing with water was performed and the proportion of aluminum in sites other than the skeleton is 8%. Further, it can be seen that in Example 5 using as a catalyst the silicate-coated MFI-type zeolite having a small particle diameter, the conversion ratio of toluene can be improved while the selectivity of p-xylene is held, as compared with Example 4 using as a catalyst the silicate-coated MFI-type zeolite having a large particle diameter.

INDUSTRIAL APPLICABILITY

As described above, the silicate-coated MFI-type zeolite, and the method of producing the silicate-coated MFI-type zeolite according to the present invention are implemented as industrial applicable embodiments, and useful in production of p-xylene by a disproportionation reaction or an alkylation reaction of an aromatic hydrocarbon (especially toluene).

The invention claimed is:

1. A method of producing a silicate-coated MFI-type zeolite comprising:
    synthesizing hydrothermally using a silica source, an aluminum source, a structure directing agent, and a fluorine source to obtain an MFI-type zeolite having a peak area ratio b'/a' of a peak b' at 2θ=8.4 to 9.7° to a peak a' at 2θ=7.0 to 8.4° in an X-ray diffraction spectrum of 1 or more; and
    coating the MFI-type zeolite with a silicate by synthesizing hydrothermally using a silica source and a structure directing agent and without using a fluorine source to obtain the silicate-coated MFI-type zeolite, wherein a peak area ratio b/a of a peak b at 2θ=8.4 to 9.7° to a peak a at 2θ=7.0 to 8.4° in an X-ray diffraction spectrum of the silicate-coated MFI-type zeolite is 1 or more and a pKa value measured by a Hammett indicator is +3.3 or more.

2. The method of producing the silicate-coated MFI-type zeolite according to claim 1, further comprising removing aluminum in sites other than a skeleton of the MFI-type zeolite.

3. The method of producing the silicate-coated MFI-type zeolite according to claim 1, further comprising:
    before the coating the MFI-type zeolite with the silicate, subjecting the MFI-type zeolite to an ion-exchange treatment to obtain the MFI-type zeolite having an amount of aluminum in sites other than a skeleton of the MFI-type zeolite of 10% or less.

* * * * *